United States Patent [19]

Terada et al.

[11] 4,254,274

[45] Mar. 3, 1981

[54] CYCLOALKYLIDENEMETHYLPHENYLA-CETIC ACID DERIVATIVES AND PROCESS FOR THE PREPARATION THEREOF

[75] Inventors: Atsusuke Terada; Shigeru Tanaka; Eiichi Misaka, all of Hiromachi, Japan

[73] Assignee: Sankyo Company Limited, Tokyo, Japan

[21] Appl. No.: 929,937

[22] Filed: Aug. 1, 1978

[30] Foreign Application Priority Data

Aug. 16, 1977 [JP] Japan .................... 52/98121

[51] Int. Cl.³ .................... C07C 69/753; C07C 59/86
[52] U.S. Cl. .................... 560/51; 562/459; 424/308; 424/317; 560/35; 260/501.1; 260/501.11

[58] Field of Search .................... 560/51, 52; 562/459; 424/308, 317

[56] References Cited

U.S. PATENT DOCUMENTS 3,729,509   4/1973   Schultz .................... 260/575 R Primary Examiner—Paul J. Killos
Attorney, Agent, or Firm—Frishauf, Holtz, Goodman & Woodward

[57] ABSTRACT

Novel 4-(2-oxo-1-cycloalkylidenemethyl)phenylacetic acid derivatives and non-toxic pharmaceutically acceptable salts thereof are useful as anti-inflammatory agents.

The compounds may be prepared by reacting a p-formylphenylacetic acid ester derivative with an enamine of cycloalkanone and hydrolyzing the resulting product, or with a cycloalkanone in the presence of a base.

23 Claims, No Drawings

CYCLOALKYLIDENEMETHYLPHENYLACETIC ACID DERIVATIVES AND PROCESS FOR THE PREPARATION THEREOF

The present invention relates to certain new cycloalkylidenemethylphenylacetic acid derivatives which are useful as anti-inflammatory agents and to processes for their preparation.

More particularly, this invention relates to novel cycloalkylidenemethylphenylacetic acid derivatives having the formula

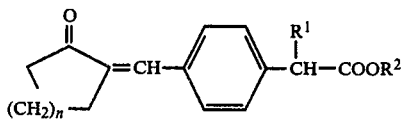

wherein $R^1$ and $R^2$ may be the same or different and each represents a hydrogen atom or a lower alkyl group, n is an integer from 1 to 3, and the non-toxic pharmaceutically acceptable salts thereof. In the above-mentioned formula (I), $R^1$ and $R^2$ can preferably represent a hydrogen atom or a straight or branched alkyl group of 1 to 4 carbon atoms such as methyl, ethyl, n-propyl, isopropyl, n-butyl or isobutyl.

More preferred compounds are those in which $R^1$ is a hydrogen atom or a methyl group, $R^2$ is a hydrogen atom, a methyl or ethyl group and n is 1 or 2. The most preferred compounds are those in which $R^1$ is methyl group, $R^2$ is a hydrogen atom and n is 1 or 2.

And further, the compound having the above formula (I) may be, if necessary, converted to the corresponding pharmaceutically acceptable salt thereof. As the salt form, there may be mentioned alkali or alkaline earth metal salts such as sodium or calcium salt; aluminum salt; ammonium salt; salts of organic bases such as triethylamine, dicyclohexylamine, dibenzylamine, morpholine, piperidine, N-ethylpiperidine; or salts of basic amino acids such as lysine or arginine.

Moreover, there are optical isomers in the compound having the above formula (I) due to the presence of an asymmetric carbon atom therein. Accordingly, the compound having the above formula (I), if formed as a mixture of such optical isomers, may be subjected to optical resolution in a conventional manner to obtain respective isomers separately. The compounds having the above formula (I) are represented herein with a single formula, including all optical isomers and a mixture thereof, but the scope of this invention is not limited with such a single representation.

The present inventors have made numerous studies on the synthetic method and pharmacological activities of cycloalkylidenemethylphenylacetic acid derivatives in order to develop anti-inflammatory agents and, as a result, found that the new phenylacetic acid derivative with a 2-oxo-1-cycloalkylidenemethyl group represented by the above formula (I) can be useful as medicaments having anti-inflammatory, analgesic and antipyretic activities.

It is, accordingly, a primary object of the present invention to provide a new class of cycloalkylidenemethylphenylacetic acid derivatives which has a utility as anti-inflammatory, analgesic and antipyretic agents.

It is another object of this invention to provide processes for the preparation of such cycloalkylidenemethylphenylacetic acid derivatives.

The compounds having the above formula (I) which may be produced according to this invention may be exemplified, for example, by the following compounds.

(1) Ethyl 2-[4-(2-oxo-1-cyclopentylidenemethyl)-phenyl[propionate
(2) 2-[4-(2-Oxo-1-cyclopentylidenemethyl)phenyl]propionic acid
(3) 4-(2-Oxo-1-cyclopentylidenemethyl)phenylacetic acid
(4) Ethyl 2-[4-(2-oxo-1-cyclohexylidenemethyl)phenyl]propionate
(5) 2-[4-(2-Oxo-1-cyclohexylidenemethyl)phenyl]propionic acid
(6) 4-(2-Oxo-1-cyclohexylidenemethyl)phenylacetic acid
(7) Sodium 2-[4-(2-oxo-1-cyclopentylidenemethyl)-phenyl]propionate
(8) Sodium 2-[4-(2-oxo-1-cyclohexylidenemethyl)-phenyl]propionate
(9) L-Arginine salt of 2-[4-(2-oxo-1-cyclopentylidenemethyl)phenyl]propionic acid
(10) L-Arginine salt of 2-[4-(2-oxo-1-cyclohexylidenemethyl)phenyl]propionic acid
(11) L-Lysine salt of 2-[4-(2-oxo-1-cyclopentylidenemethyl)phenyl]propionic acid
(12) L-Lysine salt of 2-[4-(2-oxo-1-cyclohexylidenemethyl)phenyl]propionic acid The novel compounds of this invention can be synthesized according to the processes as shown below.

PROCESS 1

The cycloalkylidenemethylphenylacetic acid derivative having the above formula (I) can be obtained by reacting a p-formylphenylacetic acid ester derivative having the formula

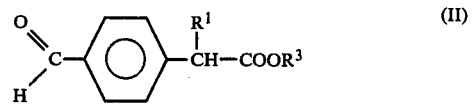

wherein $R^1$ is as defined above and $R^3$ is a lower alkyl group such as methyl, ethyl, n-propyl, isopropyl, n-butyl, isobutyl with an enamine derivative having the formula

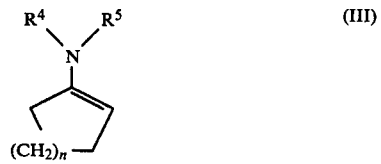

wherein $R^4$ and $R^5$ represent a lower alkyl group such as methyl, ethyl, n-propyl, isopropyl, n-butyl, isobutyl or, together with the nitrogen atom to which they are attached, may jointly form a cylic amino group optionally having a ring oxygen atom such as 1-pyrrolidinyl, piperidino. morpholino; and n is as defined above, hydrolyzing the so produced compound having the estimated structural formula represented by the formula

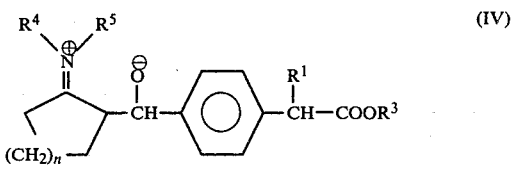

wherein $R^1$, $R^3$, $R^4$, $R^5$ and n are as defined above and, if a carboxylic acid derivative (I) wherein $R^2$ is a hydrogen atom is desired, further hydrolyzing the corresponding ester moiety.

In carrying out this process, the first reaction of the p-formylphenylacetic acid ester compound (II) with the enamine compound (III) is conducted by heating in the presence of a solvent. As the solvent which may be employed, there may be preferably mentioned aromatic hydrocarbons such as benzene, toluene, xylene, ethers such as dioxane. A reaction temperature may be between about 80° C. and 140° C., but a reflux temperature of the solvent employed is preferably employed. A reaction period of time may vary depending upon the reaction temperature and the like, but it is usually from 1 to 50 hours. After completion of the reaction, the reaction mixture may be utilized as such for the subsequent hydrolysis reaction.

The hydrolysis reaction may be effected by contacting the so obtained intermediate compound having the above formula (IV) with a hydrolyzing agent, an acid or a base. As the acid or base which may be used, there may be applied any acids or bases employable for a conventional hydrolysis reaction without any particular limitations, but there are preferably mentioned mineral acids such as hydrochloric acid, hydrobromic acid, sulfuric acid and alkali metal hydroxides such as sodium hydroxide, potassium hydroxide and the like. It is most preferable to use a mineral acid. The reaction can be usually and preferably conducted in the presence of a solvent. As the solvent which may be employed, there may be preferably used water; organic solvents, e.g. alcohols such as methanol, ethanol, n-propanol, glycols such as ethylene glycol, diethylene glycol; and a mixture thereof. A reaction temperature is not particularly critical, but the reaction is usually effected at room temperature. A reaction period of time may vary mainly depending upon the reaction temperature and the hydrolyzing agent employed, but it is usually from about 10 minutes to about 30 hours.

After completion of the reaction, the desired compound having the formula (I) wherein $R^1$ is a lower alkyl group may be recovered from the reaction mixture according to a conventional method. For instance, where a mineral acid is employed as the hydrolyzing agent, the reaction mixture is extracted with an organic solvent, e.g. benzene, the extract washed with water and dried and the solvent distilled off from the extract to afford the desired product. The product thus obtained may be purified, if necessary, by a conventional way such as vacuum distillation, column chromatography and the like when it is an oily substance.

Then, the hydrolysis reaction of the so produced ester compound may be conducted according to the process as described above with regard to the hydrolysis reaction of the compound having the above formula (IV). The reaction temperature may be preferably a reflux temperature of the solvent employed under heating and, further, both hydrolysis reactions may be concurrently accomplished under such a condition.

The desired carboxylic acid derivative thus obtained may be further purified, if desired, by a conventional method, for example, by vacuum distillation, column chromatography or recrystallization.

PROCESS 2

The cycloalkylidenemethylphenylacetic acid derivative having the above formula (I) can also be produced by reacting a p-formylphenylacetic acid ester derivative having the formula

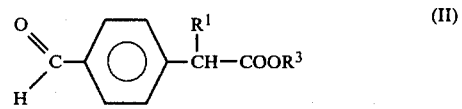

wherein $R^1$ and $R^3$ are as defined above with a cycloalkanone having the formula

wherein n is as defined above in the presence of a base.

As the base which may be employed, there may be employed any of the bases employable for a conventional alkylation reaction of an active methylene group without any particular limitations, but there may be preferably mentioned alkali metal hydroxides such as sodium hydroxide or potassium hydroxide; alkali metal alkoxides such as sodium methoxide, sodium ethoxide or potassium tert-butoxide; alkali metal amides such as sodium amide or potassium amide; alkali metal hydrides such as sodium hydride or potassium hydride and the like. The reaction is preferably effected in the presence of a solvent, and the preferable solvents may include water, alcohols such as methanol, ethanol or tert-butanol, dimethylformamide, dimethyl sulfoxide or ethers such as tetrahydrofuran or dioxane. The reaction temperature is not particularly critical, but it is usually from room temperature to around reflux temperature of the solvent employed. A reaction period of time may vary depending upon the kind of base and the reaction temperature, but it is usually 1 to 5 hours. By selecting the kind of base and solvent to be employed in this reaction, either the ester or the carboxylic acid derivative may be optionally obtained as the desired product. For instance, in the case where the alkali metal hydroxide and water are employed as the base and solvent, respectively, there can be obtained the carboxylic acid derivative, while in case of other base and organic solvent there can be obtained the ester derivative. After completion of the reaction, the desired product having the above formula (I) can be recovered from the reaction mixture by a conventional method. For instance, in the case where an aqueous solution of sodium hydroxide is employed as the base, the reaction mixture is washed with an organic solvent, e.g. ethyl acetate, an aqueous layer is made acidic with the addition of an acid, e.g. hydrochloric acid and extracted with an organic solvent, e.g., ethyl acetate, the extract is washed with water and dried and then the solvent is distilled off from the extract to give the desired product. The so obtained product may be further purified, if desired, by a conventional method such as vacuum distillation or column chromatography.

The cycloalkylidenemethylphenylacetic acid derivative having the above-mentioned formula (I) of this invention exhibits excellent anti-inflammatory, analgesic and antipyretic activities according to pharmacological tests. The results from such pharmacological tests are summarized hereinbelow.

I. Anti-inflammatory activity (I) Carrageenin Edema Test in Rats

Inflammation was introduced by injection of 0.05 ml. of 1% carrageenin suspension into the plantar tissue of rat hind paw subcutaneously, by the method of Winter et al. in Proc. Soc. Exp. Biol. Med. 111, 544 (1962). Male Wistar rats weighing 120 to 150 g. which had fasted overnight received the test drug in aqueous tragacanth suspension orally 30 minutes before the carrageenin injection.

Paw edema was measured volumetrically, just before and 3 hours after the carrageenin injection, and R (response) was obtained by the following equation: $R = (V - V_o)/V_o$, where $V_o$ and $V$ represented the paw volumes 0 and 3 hours after carrageenin injection, respectively.

(2) Adjuvant-induced Arthritis Test in Rats (Therapeutic Effect on Established Arthritis).

Female Lewis rats of 7–8 weeks old were injected intradermally in the hind paw with 0.05 mg. of heat-killed *Mycobacterium butyricum* in 0.05 ml. of liquid paraffin. Eighteen days after adjuvant injection, the well-established arthritic animals were selected and subjected to 7 days therapy with drug (twice a day orally). As the response, the volume of injected foot was measured by water displacement method at the beginning (day 18) and the end (day 25) of the therapy period.

II. Analgesic Activity on Inflammatory Pain

Thermal Pain Test in Rats

The test was conducted according to the method reported by Y. Iizuka and K. Tanaka in Folia Pharmacol. Japan, 70, 697 (1974).

Under ether anesthesia, male Wistar rat of 5–7 weeks old received a standard heat injury at the hind paw by dipping it in hot water (57° C., 6 seconds). More than 1 hour later, the pain reaction could be evoked easily by another stimulatory heat (40° C., 5 seconds). Namely immediately after this treatment, the animal used to lift up the injured paw, presumably to avoid further pain which might be caused by touching it with the wire-netting of the cage.

Thus, the sum of duration time of the paw-lifting behavior was counted over a 30 seconds period and this was used as "pain reaction time." Drug was given orally 2 hours after the first application of heat and the mean value of "pain reaction time" at 1 and 2 hours after drug administration was used as the response.

III. Antipyretic Activity

LPS-induced Fever Test in Guinea Pigs

Antipyretic activity was determined by a modified method of Kobayashi and Takagi in Jap. J. Pharmacol. 18, 80 (1968). Female Hartley guinea pigs weighing about 300 g. had fasted overnight and the fever was induced by injecting 1.0 μg/ml/kg LPS (product of Difco Laboratories, U.S.A., Lipo polysaccharide from *Escherichia coli*).

One hour after the injection, rectal temperature was measured and only the animals with fever between 0.8° C. and 1.2° C. were used for experiment.

Drugs were administered orally 1.5 hours after LPS injection, and the mean value of rectal temperature of each animal 1 and 2 hours after drug administration was used as the response.

Statistical Analysis

In order to get the regression line of H (% inhibition of the response) on D (dose of test drug), H in each animal was calculated from the ratio of the response to the mean response in non-medicated group. Then, the regression line and $ID_{50}$ were obtained by the method of least squares. The confidence limits of $ID_{50}$ was calculated using *Fieller's Equation*.

In adjuvant arthritis, however, the ratio (RR) of responses *after/before* medication period was calculated first, where the response meant the swelled foot volume of the injected foot. Then, H in each animal was calculated from the ratio of RR to RRc, where RRc represented the mean RR in non-medicated group.

The results of the above experiments are given in Tables I and II.

TABLE I

| Compounds | Anti-inflammatory activity* Inhibition % 6.3 mg/kg (P.O.) | Analgesic activity 6.3 mg/kg (P.O.) |
|---|---|---|
| Ethyl 2-[4-(2-oxo-1-cyclopentylidenemethyl)phenyl]-propionate | 85.0 | 50.5 |
| Ethyl 2-[4-(2-oxo-1-cyclohexylidenemethyl)phenyl]-propionate | 72.7 | 59.2 |
| 2-[4-(2-Oxo-1-cyclopentylidenemethyl)phenyl]-propionic acid | 76.4 | 77.4 |
| 2-[4-(2-Oxo-1-cyclohexylidenemethyl)phenyl]-propionic acid | 75.0 | 86.8 |
| (Control) Phenylbutazone | (25 mg/kg) 30.6 | (19 mg/kg) 37 |

*Carrageenin Edema Test

TABLE II

| Compounds | Anti-inflammatory activity Carrageenin Edema Test $ID_{50}$ (mg/kg, P.O.) | Anti-inflammatory activity Adjuvant Arthritis Test $ID_{50}$ (mg/kg, days, P.O.) | Analgesic activity Thermal Pain Test $ID_{50}$ (mg/kg, P.O.) | Antipyretic activity LPS-induced Fever Test $ID_{50}$ (mg/kg, P.O.) |
|---|---|---|---|---|
| 2-[4-(2-Oxo-1-cyclopentylidenemethyl)phenyl]-propionic acid | 1.4 | 1.2 | 1.3 | 0.83 |
| 2-[4-(2-Oxo-1-cyclohexylidenemethyl)phenyl]-propionic acid | 1.2 | 0.2 | 1.8 | 1.46 |
| (Control) Ibuprofen | 10.8 | 104.5 | 17.8 | 1.26 |

As clearly seen from the results of the above pharmacological tests, the compounds having the above formula (I) and pharmaceutically acceptable salts thereof are useful as analgesic and anti-inflammatory agents. For administration thereof, there may be utilized, for example, oral administration with tablets, capsules, granulates, powders or syrups or rectal administration with suppositories. Doses thereof may vary depending upon the severities, age and body weight of patients, but a daily dose for adults is usually in the range of about 50 mg to about 2000 mg and may be given in single dosage form or several divided dosage forms.

The invention thus further consists in a pharmaceutical composition comprising a compound of formula (I), as hereinbefore defined, in admixture with a pharmaceutically acceptable carrier or diluent. Known carriers or diluents may be used and these will be chosen having regard to the desired route of administration, as is well-known in the art.

The following examples are given for the purpose of a more concrete explanation of this invention.

EXAMPLE 1

Ethyl 2-[4-(2-oxo-1-cyclohexylidenemethyl)phenyl]propionate

A mixture of 5.15 g of ethyl 2-(p-formylphenyl)propionate, 4.5 g of pyrrolidinocyclohexene and 20 ml of benzene was heated under reflux for 18 hours. After cooling, the reaction mixture was admixed with a mixture of 5 ml of conc. hydrochloric acid and 5 ml of water under ice-cooling and then stirred at room temperature overnight. 100 ml of benzene were added thereto, the organic layer was separated and then washed with water. After drying over anhydrous sodium sulfate, the benzene was distilled off to leave an oily substance. The substance was distilled under reduced pressure to afford 2.3 g of the desired product as a yellow oily substance having a boiling point of 160°-170° C./0.3 mmHg (bath temp.).

Analysis for $C_{18}H_{22}O_3$: Calcd: C, 75.49; H, 7.74. Found: C, 75.08; H, 7.63.

EXAMPLE 2

Ethyl 2-[4-(2-oxo-1-cyclopentylidenemethyl)phenyl]propionate

A mixture of 5.15 g of ethyl 2-(p-formylphenyl)propionate and 4.5 g of morpholinocyclopentene in 10 ml of benzene was heated under reflux for 10 hours. After cooling, a mixture of 5 ml of conc. hydrochloric acid and 5 ml of water was added to the reaction mixture under ice-cooling and the resulting mixture was stirred at room temperature overnight. After addition of 100 ml of benzene, an organic layer was separated, washed with water and dried over anhydrous sodium sulfate. The solvent was distilled off to leave an oily substance, which was then distilled under reduced pressure to give 5.3 g of the desired product having a boiling point of 160°-165° C./0.25 mmHg.

Analysis for $C_{17}H_{20}O_3$: Calcd., C, 74.95; H, 7.40. Found, C, 74.79; H, 7.33.

EXAMPLE 3

2-[4-(2-Oxo-1-cyclopentylidenemethyl)phenyl]propionic acid

A solution of 1.4 g of ethyl 2-[4-(2-oxo-1-cyclopentylidenemethyl)phenyl]propionate in 15 ml of dioxane and 100 ml of a 10% aqueous solution of hydrogen bromide was heated under reflux for 1 hour. After cooling, the reaction mixture was extracted with ether. The extract was washed with water and dried over anhydrous sodium sulfate. The ether was distilled off to leave an oily substance, which was then vacuum distilled to afford 0.3 g of the desired product having a boiling point of 210°-215° C./0.2 mmHg (bath temp.). This product solidified and crystallized after cooling. m.p. 106°-107° C.

Analysis for $C_{15}H_{16}O_3$: Calcd: C, 73.75; H, 6.60. Found: C, 73.40; H, 6.78.

EXAMPLE 4

2-[4-(2-Oxo-1-cyclohexylidenemethyl)phenyl]propionic acid

A solution of 1.3 g of ethyl 2-(4-(2-oxo-1-cyclohexylidenemethyl)phenyl)propionate in 15 ml of dioxane and 100 ml of a 10% aqueous solution of hydrogen bromide was heated under reflux for 1 hour. After cooling, the reaction mixture was extracted with ether. The extract was washed with water and dried over anhydrous sodium sulfate. The ether was distilled off to leave an oily substance, which was then vacuum distilled to give 0.6 g of the desired product having a boiling point of 210°-215° C./0.3 mmHg (bath temp.). This product solidified and crystallized after cooling. m.p. 108°-110° C.

Analysis for $C_{16}H_{18}O_3$ Calcd., C, 74.39, H, 7.02 Found, C, 74.36, H, 7.06

EXAMPLE 5

2-[4-(2-Oxo-1-cycloheptylidenemethyl)phenyl]propionic acid

To a mixture of 5.15 g of ethyl 2-(p-formylphenyl)propionate and 4.2 g of cycloheptanone were added dropwise at room temperature 30 ml of an aqueous solution of 2.6 g of sodium hydroxide and the resulting mixture was heated under reflux for 3 hours. After cooling, the reaction mixture was extracted twice with ethyl acetate, an aqueous layer was made acidic with hydrochloric acid and extracted with ethyl acetate. The extract was washed with water and dried over anhydrous sodium sulfate. The ethyl acetate was distilled off to leave an oily substance, which was then subjected to a silica gel column chromatography and elution was effected with benzene-ethyl acetate 5:1 to yield an yellow oily substance. The substance was distilled under reduced pressure to give 2.7 g of the desired product as a pale yellow oily substance having a boiling point of 210°-215° C./0.3 mmHg (bath temp.).

Analysis for $C_{17}H_{20}O_3$: Calcd: C, 74.97; H, 7.40. Found: C, 75.20; H, 7.54.

EXAMPLE 6

Ethyl 4-(2-oxo-1-cyclopentylidenemethyl)phenylacetate

A mixture of 3.7 g of ethyl p-formylphenylacetate, 5.2 g of pyrrolidinocyclopentene and 20 ml of benzene was heated under reflux for 13 hours. After cooling, 5 ml of conc. hydrochloric acid and 5 ml of water were added to the reaction mixture and the resulting mixture was stirred at room temperature overnight. To the mixture added 100 ml of benzene, a benzene layer was separated, washed with water and dried over anhydrous sodium sulfate. Thereafter, the benzene was distilled off and the residue was subjected to a silica gel column chromatography. Elution was effected with benzene-ethyl acetate 50:1 to give an oily substance, which was then distilled under reduced pressure to afford 0.5 g of an oily substance having a boiling point of 175°–180° C./0.3 mmHg (bath temp.).

Analysis for $C_{16}H_{18}O_3$: Calcd: C, 76.57; H, 6.43. Found: C, 76.78; H, 6.50.

EXAMPLE 7

4-(2-Oxo-1-cyclopentylidenemethyl)phenylacetic acid

A mixture of 0.4 g of ethyl 4-(2-oxo-1-cyclopentylidenemethyl)phenylacetate in 100 ml of a 10% aqueous solution of hydrobromic acid and 10 ml of dioxane was heated under reflux for 1 hour. After cooling, the reaction mixture was extracted with ether, an ether layer was washed with water and dried. The ether was distilled off and the residual oily substance was distilled under reduced pressure to give 0.1 g of an oily substance having a boiling point of 205°–210° C./0.25 mmHg.

Analysis for $C_{14}H_{14}O_3$: Calcd: C, 73.02; H, 6.13. Found: C, 73.26; H, 6.44.

EXAMPLE 8

2-[4-(2-Oxo-1-cyclohexylidenemethyl)phenyl]propionic acid L-arginine salt

To a solution of 0.2 g of 2-[4-(2-oxo-1-cyclohexylidenemethyl)phenyl]propionic acid in 1.6 ml of water and 0.5 ml of acetone was added dropwise with stirring 0.5 ml of an aqueous solution of 0.13 g of L-arginine and the resulting mixture was stirred for 1 hour. Then, 10 ml of acetone were added thereto and stirring was then continued for further 3 hours. The acetone and water were distilled off to give 0.2 g of the desired product. m.p. (decomp.) 205°–215° C.

Analysis for $C_{22}H_{32}O_5N_4$: Calcd: C, 61.09; H, 7.46; N, 12.96. Found: C, 60.98; H, 7.45; N, 12.99.

What is claimed is:

1. A compound having the formula

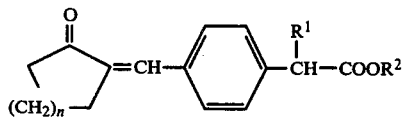

wherein R is a methyl group, $R^2$ is a hydrogen atom or an alkyl group having from 1 to 4 carbon atoms, n is an integer from 1 to 2, and non-toxic pharmacetutically acceptable salts thereof.

2. The compound of claim 1 wherein $R^1$ is a methyl group, $R^2$ is a hydrogen atom, or a methyl or ethyl group, and n is 1.

3. The compound of claim 1 wherein $R^1$ is a methyl group, $R^2$ is a hydrogen atom and n is 1 or 2.

4. The compound of claim 1 which is ethyl 2-[4-(2-oxo-1-cyclopentylidenemethyl)phenyl]propionate.

5. The compound of claim 1 which is 2-[4-(2-oxo-1-cyclopentylidenemethyl)phenyl]propionic acid.

6. The compound of claim 1 which is ethyl 2-[4-(2-oxo-1-cyclohexylidenemethyl)phenyl]propionate.

7. The compound of claim 1 which is 2-[4-(2-oxo-1-cyclohexylidenemethyl)phenyl]propionic acid.

8. The compound of claim 1 which is sodium 2-[4-(2-oxo-1-cyclopentylidenemethyl)phenyl]propionate.

9. The compound of claim 1 which is sodium 2-[4-(2-oxo-1-cyclohexylidenemethyl)phenyl]propionate.

10. The compound of claim 1 which is L-arginine salt of 2-[4-(2-oxo-1-cyclopentylidenemethyl)phenyl]-propionic acid.

11. The compound of claim 1 which is L-arginine salt of 2-[4-(2-oxo-1-cyclohexylidenemethyl)phenyl]propionic acid.

12. The compound of claim 1 which is L-lysine salt of 2-[4-(2-oxo-1-cyclopentylidenemethyl)phenyl]propionic acid.

13. The compound of claim 1 which is L-lysine salt of 2-[4-(2-oxo-1-cyclohexylidenemethyl)phenyl]propionic acid.

14. A pharmaceutical composition comprising a compound according to any one of claims 1 to 5, 6, 7, and 8 to 13 in admixture with a pharmaceutically acceptable carrier or diluent.

15. The compound of claim 1 wherein $R^1$ is a methyl group, $R^2$ is a hydrogen atom or a methyl or ethyl group, and n is 2.

16. The salt of the compound of any one of claims 1, 2, 3, 5, 7 and 15, wherein said salt is selected from the group consisting of the sodium, calcium, aluminum, triethylamine, dicyclohexylamine, dibenzylamine, morpholine, piperidine, N-ethylpiperidine, lysine and arginine salts.

17. The salt of claim 16, wherein said salt is the calcium salt.

18. The method of alleviating at least one symptom selected from the group consisting of inflammation, pain or fever, comprising administering to a host having inflammation, pain or fever symptoms, an amount of a compound or salt as claimed in any one of claims 2, 3, 4, 5, 6, 7, 8, 9, 10, 11, 12 and 15 sufficient to alleviate said symptoms.

19. The method of alleviating at least one symptom selected from the group consisting of inflammation, pain or fever, comprising administering to a host having inflammation, pain or fever symptoms, an amount of a salt as claimed in claim 16 sufficient to alleviate said symptoms.

20. The method of alleviating at least one symptom selected from the group consisting of inflammation, pain or fever, comprising administering to a host having inflammation, pain or fever symptoms, an amount of a salt as claimed in claim 17 sufficient to alleviate said symptoms.

21. The method of alleviating at least one sympton selected from the group consisting of inflammation, pain or fever, comprising administering to a host having inflammation, pain or fever symptoms, an amount of the following compound or salts sufficient to alleviate said symptoms:

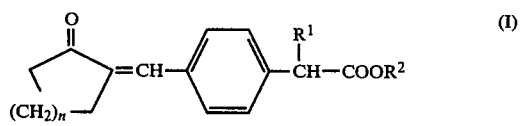

wherein $R^1$ is an alkyl group having from 1 to 4 carbon atoms, $R^2$ is a hydrogen atom or an alkyl group having from 1 to 4 carbon atoms, n is an integer from 1 to 2, and non-toxic pharmaceutically acceptable salts thereof.

22. The method of claim 21 wherein said compound is a salt selected from the group consisting of the sodium, calcium, aluminum, triethylamine, dicyclohexylamine, dibenzylamine, morpholine, piperidine, N-ethylpiperidine, lysine and arginine salts.

23. The salt of claim 22 wherein said salt is the calcium salt.

* * * * *